United States Patent [19]
Kelley et al.

[11] Patent Number: 5,672,344
[45] Date of Patent: Sep. 30, 1997

[54] VIRAL-MEDIATED GENE TRANSFER SYSTEM

[75] Inventors: William N. Kelley; Thomas D. Palella; Myron Levine, all of Ann Arbor, Mich.

[73] Assignee: The Regents of the University of Michigan, Ann Arbor, Mich.

[21] Appl. No.: 194,794

[22] Filed: Feb. 10, 1994

Related U.S. Application Data

[63] Continuation of Ser. No. 737,035, Jul. 29, 1991, abandoned, which is a continuation of Ser. No. 139,597, Dec. 30, 1987, abandoned.

[51] Int. Cl.$^6$ .......................... A61K 48/00; C12N 15/86
[52] U.S. Cl. .................... 424/93.2; 424/93.6; 435/172.3; 435/320.1; 435/368
[58] Field of Search ................. 435/69.1, 320.1, 435/172.1, 172.3, 368, 325, 366; 424/93.2, 93.6

[56] References Cited

U.S. PATENT DOCUMENTS

| | | | |
|---|---|---|---|
| 4,396,601 | 8/1983 | Selser et al. | 424/94.5 |
| 4,403,035 | 9/1983 | Anderson et al. | 435/172.3 |
| 4,497,796 | 2/1985 | Selser et al. | 514/44 |
| 4,579,821 | 4/1986 | Palmiter et al. | 435/172.3 |
| 4,680,176 | 7/1987 | Berns et al. | 424/205.1 |
| 4,703,011 | 10/1987 | Kit et al. | 435/236 |
| 4,704,362 | 11/1987 | Itakura et al. | 435/252.3 |
| 5,288,641 | 2/1994 | Roizman | 435/320.1 |
| 5,599,691 | 2/1997 | Roizman | 435/69.1 |

OTHER PUBLICATIONS

Tackney et al., "Transduction of the Chinese Hamster Ovary aprt Gene by Herpes Simplex Virus", J. Virol., vol. 52, No. 2, pp. 606–614 Nov. 1984.
"Report and Recommendations of the Panel to Assess the NIH Investment in Research on Gene Therapy", Eds. S.H. Orkin and A.G. Arno Dec. 1995.
Kit, Microbiological Sciences, vol. 2, No. 12, 1985 369–375.
Shih et al., 1984, PNAS 81:5867–5870.
Kwong et al, 1984, J. Virol., 51:595–603.
Wolfe et al., "Herpesvirus vector gene transfer and expression of β-glucuronidase in the central nervous system of MPS VII mice" Nature Genetics (1992) 1:379–384.
Andersen et al., "Gene transfer into mammalian central nervous system using herpes virus vectors: extended expression of bacterial lacZ in neurons using the neuron-specific enolase promoter" Hum. Gene Ther. (1992) 3:487–499.
Ragot et al., "Efficient adenovirus-mediated transfer of a human minidystrophin gene to skeletal muscle of mdx mice" Nature (1993) 361:647–650.
La Salle et al., "An adenovirus vector for gene transfer into neurons and glia in the brain" Science (1993) 259:988–990.

Anderson, "Prospects for human gene therapy" Science (1984) 226:401–409.
Friedmann, "Progress toward human gene therapy" Science (1989) 244:1275–1281.
Anderson, "Human gene therapy" Science (1992) 256:808–813.
Centelles et al., "Is adenosine–deaminase involved in adenosine transport?" Med. Hypotheses (1990) 33:245–250.
Jiao et al., "Persistence of plasmid DNA and expression in rat–brain cells in vivo" Exper. Neur. (1992) 115:400–413.
Schwandt et al., "Genetic–disorders of metabolism in adults" Internist (1989) 30:547–555. A partial list of translated English descriptors is included herewith.
Hidaka et al., "Expression of human hypoxanthine–guanine phosphoribosyltransferase messenger–RNA in brains of mice infected with a recombinant herpes–simplex virus Type–1" Clin. Res. (1989) 37:A600–A600.
Albertini et al., "In vivo somatic mutations in humans: measurement and analysis" Ann. Rev. Genet. (1990) 24:305–326.
Skopek et al., "Molecular analyses of a Lesch–Nyhan syndrome mutation (hprt$_{Montreal}$) by use of lymphocyte–T cultures" Hum. Gen. (1990) 85:111–116.
Rossi et al., "Mutations affecting RNA splicing in man are detected more frequently in somatic than in germ–cells" Mut. Res. (1990) 244:353–357.
Wilson et al., "Prospects for gene therapy of familial hypercholesterolemia" Mol. Biol. Med. (1990) 7:223–232.
Stratford–Perricaudet et al., "Evaluation of the transfer and expression in mice of an enzyme–encoding gene using a human adenovirus vector" Hum. Gene Ther. (1990) 1:241–256.
Breakefield et al., "Herpes simplex virus for gene delivery to neurons" New Biol. (1991) 3:203–218.
Nabel et al., "Gene transfer into vascular cells" J. Am. Coll. Cardiol. (1991) 17:189B–194B.

(List continued on next page.)

Primary Examiner—David Guzo
Attorney, Agent, or Firm—Morrison & Foerster LLP

[57] ABSTRACT

A recombinant neurotropic HSV-1 vector carrying the gene for human HPRT under the direction of the viral TK promoter expresses a high level of human enzyme in host neuronal cells, yet has reduced cytopathicity. The virulence of the HSV-1 vector is further reduced by rendering it replication-defective through UV-irradiation or the use of a replication-defective HSV-1 deletion mutant in its construction. The recombinant vector is also provided with a non-vital site of initiation of DNA synthesis, which permits the HPRT gene to replicate independently of the viral genome, thus providing means for amplification of the gene in the host. The recombinant HSV-1 vector's high level of expression of HPRT coupled with decreased virulence allows treatment of HPRT deficieny by direct infection of the host organism.

35 Claims, 1 Drawing Sheet

OTHER PUBLICATIONS

Johnson et al., "Effects of gene transfer into cultured CNS neurons with a replication–defective herpes simplex virus Type 1 vector" *Mol. Brain Res.* (1992) 12:95–102.

Grossman et al., "Frontiers in gene therapy: LDL receptor replacement for hypercholesterolemia" *J. Lab. Clin. Med.* (1992)5:457–460.

Davidson et al., "Human hypoxanthine–guanine phosphoribosyltransferase deficiency: the molecular defect in a patient with gout ($HPRT_{ASHVILLE}$)" *J. Biol. Chem.* (1989) 264:520–525.

Davidson et al., "Hypoxanthine–guanine phosphoribosyltransferase: genetic evidence for identical mutations in two partially deficient subjects" *J. Clin. Invest.* (1988) 82:2164–2167.

Davidson et al., "Molecular basis of hypoxanthine–guanine phosphoribosyltransferase deficiency in ten subjects determined by direct sequencing of amplified transcripts" *J. Clin. Invest.* (1989) 342–346.

Coen et al., "Thymidine kinase–negative herpes simplex virus mutants establish latency in mouse trigeminal ganglia but do not reactivate" *Proc. Natl. Acad. Sci. USA* (1989) 86:4736–4740.

Dialog™ abstract of Hochstenbach et al., "Endoplasmic reticulum resident protein of 90 kilodaltons associates with the T and B–cell antigen receptors and major hisocompatibility complex antigens during their assembly" *Proc. Natl. Acad. Sci. USA* (1992) 89:4734–4738.

Sankaranarayanan, "Ionizing radiation and genetic risks. I. Epidemiological, population genetic, biochemical and molecular aspects of mendelian diseases" *Mut. Res.* (1991) 258:3–49.

Gibbs et at., "Identification of mutations leading to the Lesch–Nyhan syndrome by automated direct DNA sequencing of in vitro amplified cDNA" *Proc. Natl. Acad. Sci. USA* (1989) 86:1919–1923.

de Boer et al., "Mutational analysis of the structure and function of the adenine phosphoribosyltransferase enzyme of Chinese hamster" *J. Mol Biol.* (1991) 221:163–174.

Zhang et al., "Spectrum of spontaneously occurring mutations in the hprt of V79 Chinese hamster cells" *J. Mol. Biol.* (1992) 223:627–635.

Jansen et al., "The gene encoding hypoxanthine–guanine phosphoribosyltransferase as target for mutational analysis: PCR cloning and sequencing of the cDNA from the rat" *Mut. Res.* (1992) 266:105–116.

Gordon et al., "The molecular characterization of $HPRT_{CHERMSIDE}$ and $HPRT_{COORPAROO}$: two Lesch–Nyhan patients with reduced amounts of mRNA" *Gene* (1991) 108:299–304.

Thompson et al., "Biological characterization of a herpes simplex virus intertypic recombinant which is completely and specifically non–neurovirulent" *Virology* (1983) 131:171–179.

Schröder et al., "Neuropathogenicity of herpes simplex in mice: protection against lethal encephalitis by co–infection with a non–encephalitogenic strain" *J. Gen. Virol.* (1983) 64:1973–1982.

Glorioso et al., "Immunogenicity of herpes simplex virus glycoproteins gC and gB and their role in protective immunity" *Jrnl. Virol.* (1984) 50:805–812.

Thompson et al., "Vaccine potential of a live avirulent herpes simplex virus" *Microbial. Pathogen.* (1986) 1:409–416.

Kümel et al., "Neurovirulence and latency in inbred mice of two HSV–1 intrastrain variants of divergent pathogenicity" *Med. Microbiol. Immunol.* (1986) 174:313–324.

Javier et al., "Genetic and biological analyses of a herpes simplex virus intertypic recombinant reduced specifically for neurovirulence" *J. Virol.* (1987) 61:1978–1984.

Kelley, W.N. "Evolution of Molecular Biology: The Future Role for the Clinical Investigator and the ABIM" from the 50th Anniversary Symposium and Celebration of the American Board of International Medicine (1987).

Kelley, W.N. et al., "The Jeremiah Metzger Lecture—Current Status of Human Gene Therapy", *Transactions of Am. Clin. Climatolog. Assoc.* vol. 99:152–169 (1987).

Hamer, D.H, "DNA Cloning in Mammalian Cells with SV40 Vectors," *Genetic Engineering: Principles and Methods* J.K. Setlow and A. Hollander, Eds. (Plenum Press N.Y.) vol. 2:83–101 (1980).

Berkner, K.L., "Development of Adenovirus Vectors for Expression of Heterologous Genes," *BioTechniques* 6:616–629 (1988).

Morin, J.E., et al., "Recombinant Adenovirus Induces antibody Response to Hepatitis B Virus Surface Antigen in Hamster," *PNAS (USA)* 84:4626–4630 (1987).

Gluzman and Hughes, Viral Vectors (Cold Spring Harbor Laboratory, Cold Spring Harbor N.Y. (1988).

"Human hypoxanthine–guanine phosphoribosyltransferase: a single substitution in cDNA clons isolated from a patient with Lesch–Nyhan syndrome ($HPRT_{Midland}$)", Beverly L. Davidson, Thomas D. Palella and William N. Kelley, Gene 68: 85–91 (1988).

"Expression of human Hprt mRNA in brains of mice infected with a recombinant herpes simplex virus–1 vector" Thomas D. Palella et al., Gene 80: 137–144 (1989).

"An initiation site of DNA replication with transcriptional enhancer activity present upstream of the c–myc gene", Iguchi–Ariga, S.M.M. et al., The EMBO Journal vol. 7 No 10, pp. 3135–3142 (1988).

Palella, et al. "Herpes Simplex Virus–Mediated Human Hypoxanthine–Guanine Phosphoribosyltransferase Gene Transfer into Neuronal Cells", Mol Cell. Biol., vol. 8, No. 1 (in press Jan. 1988).

DeLuca, et al. "Isolation and Characterization of Deletion Mutants of Herpes Simplex Virus Type 1 in the Gene Encoding Immediate–Early Regulatory Protein ICP4", J. Virol., vol. 56, No. 2, pp. 558–570 (1985).

Munyon, et al., "Transfer of Thymidine Kinase to Thymidine Kinasless L Cells by Infection with Ultraviolet–Irradiated Herpes Simplex Virus", J. Virol. vol. 7 No. 6, pp. 813–820 (1971).

Brennand, et al., "Expression of Human and Chinese Hamster Hypoxanthine–guanine Phosphoribosyltransferase cDNA Recombinants in Cultured Lesch–Nyhan and Chinese HampsterFibroblasts", J. Bio. Chem., vol. 258, No. 16, pp. 9593–9596 (1983).

Ariga, et al. "Autonomous Replicating Sequences from Mouse Cells Which Can Replicate in Mouse Cells in Vivo and In Vitro", Mol. Cell. Biol., vol. 7, No. 1, pp. 1–6 (Jan. 1987).

Miller, et al. "Expression of a Retrovirus Encoding Human HPRT in Mice", Science vol. 225, pp. 630–632 (1984).

Miller, et al. "A transmissible retrovirus expressing human hypoxanthine phosphoribosyltransferase (HPRT): Gene transfer into cells obtained from humans deficient in HPRT", PNAS USA, vol. 80, pp. 4709–4713 (1983).

Chang, et al. "Construction of a Defective Retrovirus Containing the Human Hypoxanthine Phosphoribosyltransferase cDNA and Its Expression in Cultured Cells and Mouse Bone Marrow", Mol. Cell. Biol., vol. 7, No. 2, pp. 854–863 (Feb. 1987).

Gruber, et al. "Retroviral Vector–Mediated Gene Transfer into Human Hematopoiet Progenitor Cells", Science vol. 230, pp. 1057–1060A (Nov. 1985).

Roizman, et al., "Genetic Engineering of Novel Genomes Large DNA Viruses", Science, vol. 229, pp. 1208–1214 (Sep. 1985).

Cline, "Perspectives for Gene Therapy: Inserting New Genetic Information into Mammalian Cells by Physical Techniques and Viral Vectors" Pharmac. Ther., vol. 29, pp. 69–92 (1985).

Gilboa, et al. "Transfer and Expression of Cloned Genes Using Retroviral Vectors", BioTechniques, vol. 4, No. 6, pp. 504–512 (1986).

Williams, et al. "Somatic Gene Therapy: Current Status and Future Prospects", J. Clin. Invest., vol. 77, pp. 1053–1056 (Apr. 1986).

Shapiro, et al., "New Frontiers in Genetic Medicine", Annals of Internal Medicine, vol. 104, No. 4, pp. 527–539 (Apr. 1986).

Wilson, et al. "A Molecular Survey of Hypoxanthine–Guanine Phosphoribosyltransferase Deficiency in Man" J. Clin. Invest., vol. 7, pp. 188–195 (Jan. 1986).

Wilson, et al. "Hypoxanthine–Guanine Phosphoribosyltransferase Deficiency", N.E J. of Med., vol. 309, pp. 900–910 (Oct. 1983).

Wilson, et al. "Human Hypoxanthine–Guanine Phosphoribosyltransferase–Purification and Characterization of Mutant Forms of the Enzyme", J of Bio. Chem., vol. 256, No. 20, pp. 10306–10312 (1981).

Holden, et al. "Human Hypoxanthine–Guanine Phosphoribosyltransferase–Evidence for Tetrameric Structure", J. of Bio. Chem., vol. 253, No. 12, pp. 4459–4463 (1978).

Davidson et al., "Human hypoxanthine–guanine phosphoribosyltransferase: a single nucleotide substitution in cDNA clones isolated from a patient with Lesch–Nyhan syndrome (HPRT$_{Midland}$)" Gene (1988) 68:85–91).

Muzyczka et al., "Use of adeno–associated virus as a mammalian transduction vector" Curr. Comm. Mol. Biol., Viral Vectors, Gluzman et al., eds., (1988) pp. 39–44.

Hughes, "Introduction" Curr. Comm. Molecular Biol., Viral Vectors, Gluzman et al., eds., (1988) pp. 1–12.

Ho et al., "β–Galactosidase as a marker in the peripheral and neural tissues of the herpes simplex virus–infected mouse" Virology (1988) 167:279–283.

Dobson et al., "A latent, nonpathogenic HSV–1–derived vector stably expesses β–galactosidase in mouse neurons" Neuron (1990) 5:353–360.

Chiocca et al., "Transfer and expression of the lacZ gene in rat brain neurons mediated by herpes simplex virus mutants" The New Biologist (1990) 2:739–746.

Rosenfeld et al., "Adenovirus–mediated transfer of a recombinant α1–antitrypsin gene to the lung epithelium in vivo" Science (1991) 252:431–434.

Rosenfeld et al., "In vivo transfer of the human cystic fibrosis transmembrane conductance regulator gene to the airway epithelium" Cell (1992) 68:143–155.

Fink et al., "In vivo expression of β–galactosidase in hippocampal neurons by HSV–mediated gene transfer" Hum. Gene Ther. (1992) 3:11–19.

and, et al., "A Transmissible Retrovirus Expressing
VIRAL-MEDIATED GENE TRANSFER SYSTEM This is a continuation division of U.S. patent application Ser. No. 07/737,035, filed Jul. 29, 1991, entitled "Viral-Mediated Gene Transfer System," by William N. Kelley et al., now abandoned, which is a continuation of U.S. patent application Ser. No. 07/139,597, filed Dec. 30, 1987, now abandoned.

The present invention generally comprises a viral-mediated gene transfer system for the delivery of a human gene to a selected cell or tissue and its expression therein useful for therapeutic purposes. The gene transfer system of the present invention comprises a recombinant viral vector which exhibits both a decreased level of virulence, and a high level of expression of the delivered gene. The viral vector of the invention provides for amplification of the gene independent of replication of the viral genome.

BACKGROUND OF THE INVENTION

The present invention relates generally to the transfer of genetic information, and, more specifically, to a viral-mediated gene transfer system for the delivery of a human gene to a selected host cell or tissue and its expression therein.

The enormous potential of gene therapy for the treatment of inherited and acquired diseases has led to the development of several methods for introducing new genetic information into cells. One widely used method for the transfer of genetic information into cells in vitro is transfection using calcium phosphate coprecipitation to facilitate the uptake and stable integration of exogenous DNA by the cell. An alternative method for cells not particularly susceptible to DNA uptake by calcium phosphate coprecipitation involves their fusion with liposomes, erythrocyte ghosts or spheroplasts into which the desired DNA has been incorporated. However, these methods of DNA transfer have a low degree of efficiency of DNA uptake and are not particularly useful outside the laboratory setting.

Attempts to develop alternative methods for the transfer of genetic information have led to the derivation of vectors from DNA and RNA viruses which can carry or "vector" exogenous genetic material into a host cell through infection. The term "viral vector", as used herein, refers to a virus used for the transfer of an exogenous nucleic acid sequence inserted into its genome. Since DNA viruses have generally been considered too virulent for practical application, recent efforts have focused on the RNA retrovirus.

Retroviruses are RNA viruses with relatively small and well-characterized dimeric genomes. After penetrating the host cell during infection, the retrovirus integrates its genetic information with that of the host by inserting a reverse transcript (the provirus) of its RNA genome into the host cell's genome during replication of the host DNA. By inserting an RNA gene or an RNA transcript of a DNA gene into the retroviral genome prior to infection of the host cell, the recombinant virus can be used to deliver and integrate the gene into the host genome. The term "gene transfer" refers to the transfer of DNA and RNA genes and, for the sake of simplicity, when applied herein to RNA viral vectors, also refers to the transfer of an RNA transcript of a DNA gene. By the term "gene delivery" is meant the transfer of a gene into a host cell or organism with or without integration into the host genome.

Retroviral vectors have been constructed for a variety of genes. For example, retroviral vectors capable of expressing exogenous human genes in human fibroblasts and lymphoblasts in vitro have been constructed and are described in Miller, A. D., et al. "A Transmissible Retrovirus Expressing Human Hypoxanthine Phosphoribolsyltransferase (HPRT): Gene Transfer into Cells Obtained from Humans Deficient in HPRT", PNAS USA, Vol. 80, pp. 4709–4713 (1983). Since continued replication of infectious virus particles in the host cell may be deleterious to the host, replication-defective retroviruses which will not proliferate in the host cell after infection have also been employed in the construction of retroviral vectors, for example as described by Gruber, H. E. et al, "Retroviral Vector-Mediated Gene Transfer into Human Hematopoietic Progenitor Cells", Science, Vol. 230, pp. 1057–1060 (1985), and as generally described by Gilboa, E. et al; "Transfer and Expression of Cloned Genes Using Retroviral Vectors, BioTechniques, Vol. 4, No. 6, pp. 504–512 (1986).

However, retroviral vector constructs in general suffer from a low efficiency of integration into the host genome, thus necessitating hyperinfection of the host to achieve adequate levels of gene expression. Postinfection amplification of the gene in the host has not been considered a feasible method of enhancing expression since replication of the retrovital genome would also be required to replicate the gene. Thus, in replication-defective retroviral vectors, viral-dependent amplification of the gene cannot be achieved and, in replication-competent vectors, amplification of the gene would result in undesired replication of the viral genome. It would thus be desirable to provide means for amplification of the gene delivered to the host which is independent of replication of the viral genome. The gene transfer system of the present invention provides for amplification of the gene which is independent of viral replication.

The low efficiency of retroviral integration has also posed significant problems in the use of retroviral vectors for gene therapy of intact mammals. As noted above, hyperinfection of the host is generally required to achieve adequate levels of retroviral infection and gene expression. Direct hyperinfection of a host organism in vivo is not, however, desirable since such hyperinfection may be deleterious to the organism. Thus, retroviral-mediated gene therapy must generally proceed through a more circuitous route of in vitro infection. Renewable cell populations, such as those of the hematopoietic system, are removed from the host organism, and the removed cells hyperinfected in vitro by the retroviral vector carrying the desired gene. The cells thus treated are then selected for expression of the desired gene and reintroduced into the host organism. This indirect method of gene therapy is not only cumbersome and fraught with the potential for error with each additional step but, as yet, has also resulted in only transient expression of gene activity in vivo. See, for example the retroviral therapy scheme described by Miller, A. D., et al, "Expression of a Retrovirus Encoding Human HPRT in Mice," Science, Vol. 225, pp. 630–632 (1984). The viral-mediated gene transfer system of the present invention overcome these problems by providing a method of gene therapy through direct infection.

An additional problem with retroviral-mediated gene therapy is that its use is limited to renewable cell populations capable of in vitro growth and reintroduction into the host. Furthermore, the use of retroviral therapy is limited to diseases in which restoration of gene activity in these types of cells will have the desired therapeutic effect on the host organism. For example, retroviral-mediated gene therapy may not be effective for the treatment of diseases which affect non-renewable cell populations, such as neuronal cells of the central nervous system, as is the case, for example, in Lesch-Nyhan syndrome.

Lesch-Nyhan syndrome is a devastating neurological disease which is caused by a lack of activity of the human prime salvage enzyme hypoxanthine-guanine phosphoribosyltransferase (EPRT). Treatment of Lesch-Nyhan appears to require restoration of RPRT activity in the cells of the central nervous system since restoration of HPRT activity in the circulation by either exchange transfusion or bone marrow transplantation has had no demonstrable effect on neurological function. However, removal and reintroduction of cells of nondividing neuronal cells for retroviral gene therapy is clearly not feasible. Thus targeting of the HPRT gene directly to neuronal cells in vivo appears to be essential for treatment of this disease.

Because of the above-described shortenings of retroviral-mediated gene transfer, an alternative strategy for gene transfer is highly desirable. The gene transfer system of the present invention provides an alternative strategy for the delivery and expression of human genes.

One aspect of the viral-mediated gene transfer system of the present invention is an adequate level of expression of the gene after transfer to a selected cell or tissue.

An additional aspect of the viral-mediated gene transfer system of the present invention is that it requires a relatively low dose of viral vector for an adequate level of expression of the gene.

Another aspect of the viral-mediated gene transfer system of the present invention is that it utilizes a hypovirulent viral component.

Still another aspect of the viral-mediated gene transfer system of the present invention is that a gene can be effectively and directly delivered into selected cells or tissues, both in vitro and in vivo, without resorting to removal from and reintroduction of cell populations into the host organism.

An additional aspect of the gene transfer system of the present invention is that replication of the gene in the host cell can occur independently of the replication of the viral genome.

Yet another aspect of the viral-mediated gene transfer system of the present invention is that it can be directed to particular cells or tissues for which it exhibits tropism.

The present invention provides a viral-mediated gene transfer system which exhibits a high level of expression, a low level of virulence and provides means for amplification of the gene independent of replication of the viral genome. Delivery and expression of the gene by the transfer system of the present invention is useful for therapeutic purposes, and can be used for gene therapy by direct infection of a host organism.

SUMMARY OF THE INVENTION

The present invention generally comprises a viral-mediated gene transfer system for the delivery of a human gene into a selected cell or tissue and its expression therein. The gene transfer system of the present invention further comprises a recombinant viral vector which exhibits both a decreased level of virulence, and a high level of expression of the delivered gene. The vector of the invention further provides means for autonomous amplification of the delivered gene and can be used for gene therapy by direct infection of a host organism.

The viral-mediated gene transfer system of the present invention comprises a DNA viral genome to which a human gene, together with any promoter or regulatory elements necessary for its expression in the selected cell or tissue, is operatively linked. By human gene is meant any sequence of nucleic acids or reverse transcript thereof which codes for a polypeptide present in the human population or which can function as a regulatory element in the human population, or both. This term includes naturally-occurring sequences present in vivo, as well as synthetic or any coding sequences which are capable of expression.

Virulence of the viral vector of the invention is reduced by virtue of the position of the insertion of the human gene into the viral genome, and is further decreased by genetic manipulation or mutagenic treatment of the vital genome to render it replication-defective. Expression of the gene delivered by the vector of the invention is enhanced by providing the vector with a nonviral site of initiation of DNA synthesis, rendering replication and amplification of the delivered gene independent of replication of the viral genome.

DESCRIPTION OF PREFERRED EMBODIMENTS OF THE INVENTION

Figure 1:
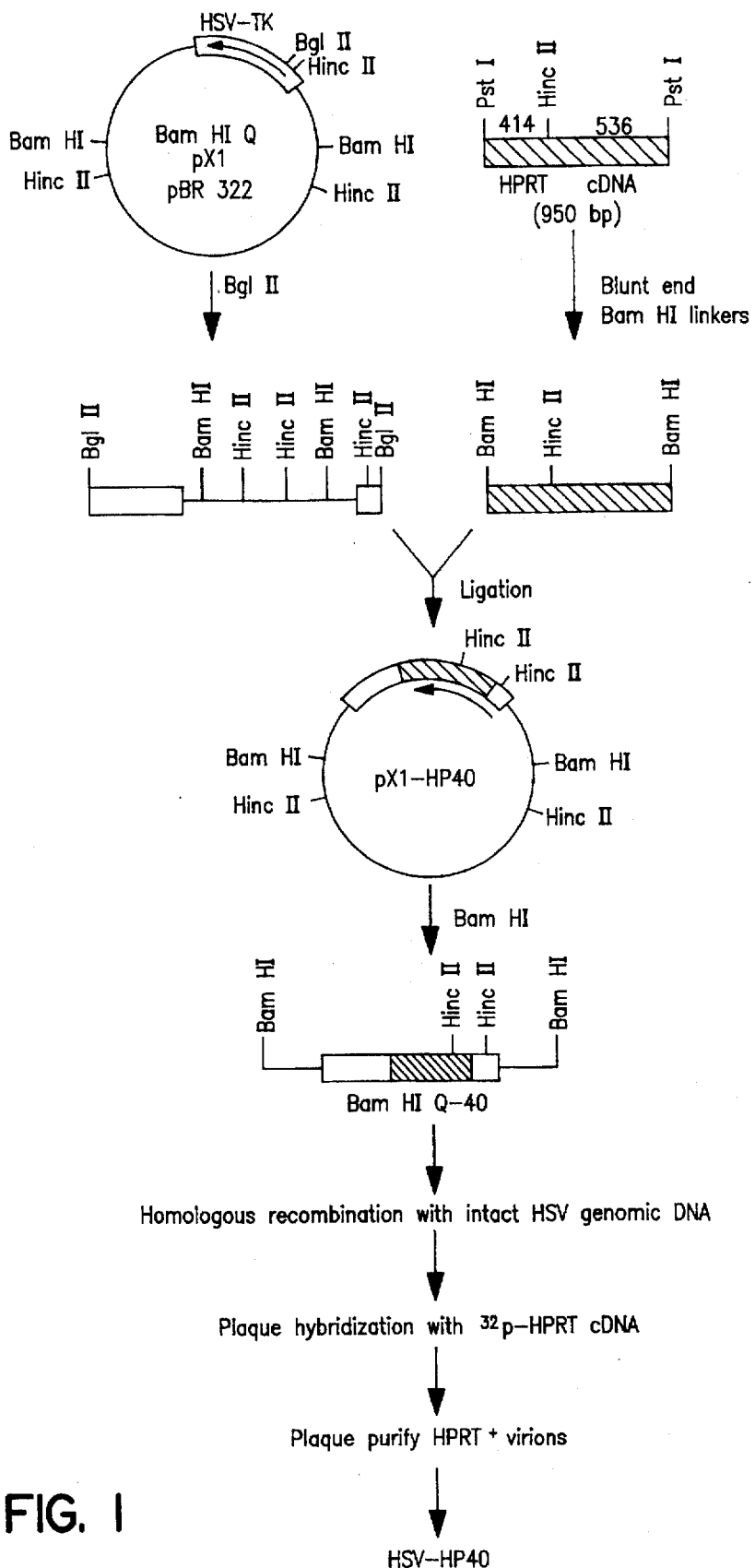
FIG. 1 is a schematic representation of the construction of a recombinant HSV-1 vector carrying the minigene for human HPRT.

A viral vector exemplifying the gene transfer system of the present invention is exemplified by a recombinant viral vector constructed by recombining a double stranded DNA viral genome with a gene coding for a detectable human protein and a promoter sequence capable of promoting expression of the human gene in the host. Preferably the viral vector of the invention further includes a nonviral site of initiation of DNA synthesis for amplification of the gene. The DNA virus of an exemplary recombinant vector of the invention is tissue-tropic to allow directing of the viral vector into the appropriate cells or tissue, the gene codes for an enzyme which can be selected for in culture, and the nonviral site of initiation of DNA synthesis is provided on a autonomous replicating DNA sequence.

The components selected for a specific example of a recombinant viral vector the present invention are the DNA neurotropic herpes simplex virus-type 1 (HSV-1), the gene for the human purine salvage enzyme hypoxanthine-guanine phosphoribosyltransferase (HPRT), the HSV-1 viral thymidine kinase (TK) promoter, and the murine autonomous replication sequence (ARS). It should be appreciated, however, that although HSV-1, HPRT, the viral TK promoter and the murine ARS were chosen as components for an exemplary viral vector of the invention, they are illustrative of an embodiment of the invention and are not intended to limit the gene transfer system of the invention to the particular components herein described.

The HPRT gene and enzyme have been used extensively in both retroviral-mediated and other exemplary gene transfer systems. The HPRT scheme is particularly attractive because the HPRT gene has been sequenced, its gene product well-characterized, and selection strategies for cells expressing this gene have already been developed. The HPRT gene is also of clinical significance because a severe deficiency of HPRT activity in humans results in Lesch-Nyhan syndrome, a devastating disease in which overproduction of uric acid and severe neurological disfunction occur.

The neurotropic herpes simplex virus-type 1 (HSV-1) establishes a latent infection in neuronal cells, can thus establish a nonlyric relationship with the host cell, and has previously been shown capable of expressing foreign genes, including Elian genes, inserted into its genome in a variety of cell culture systems. HSV-1 is an appropriate viral component of an HPRT vector of the invention because, as discussed previously, restoration of HPRT activity apparently requires the targeting of the HPRT gene to the central nervous system in order for treatment to be effective.

The HSV-1 thymidine kinase (TK) promoter has previously been shown to promote expression of foreign viral and eucaryotic genes in chimaeric herpes simplex virus constructs. The murine autonomous replication sequence (ARS) has been shown to provide a site of initiation of DNA synthesis and to amplify itself and contiguous sequences thereto.

Construction of an exemplary recombinant vector of the present invention is accomplished by selectively splicing a duplex of complementary DNA (hereinafter "cDNA") coding for human HPRT into a plasmid carrying a fragment of the HSV-1 genome with the vital thymidine kinase (TK) gene and TK promoter thereon. As shown generally in the Figure and described more specifically in the Specific Examples, the insertion of the HPRT cDNA in the plasmid yields a contiguous TK promoter-HPRT cDNA sequence, hereinafter referred to as the HPRT "minigene". The plasmid containing the HPRT minigene and intact wild type HSV-1 DNA are used to cotransfect Veto cells, and recombinant HSV-1 viruses containing the HPRT minigene are isolated therefrom. The recombinant viral vector expresses EPRT enzyme in HPRT⁻ host cells in amounts approaching or in excess of HPRT levels of normal cells, yet has mildly to moderately reduced virulence due to the position of insertion of the HPRT minigene plasmid into the thymidine kinase gene of the wild type genome. The expression of the human HPRT enzyme in rat neuronal cells also indicates that expression of the gene is not limited to the species from which it is derived.

The virulence of the vector of the invention is further reduced by constructing a replication-defective recombinant vector carrying the HPRT minigene. One approach, as detailed in Specific Example 2 is to treat the above-described HSV-1 vector carrying the HPRT minigene with UV-irradiation to render the vector replication-defective. An alternative method is to recombine the plasmid fragment containing the HPRT minigene with a replication-defective HSV-1 deletion mutant by cotransfection of an appropriate helper or packaging cell line and isolating recombinant replication-defective HSV-1 therefrom as described in Specific Example 2.

The recombinant viral vector of the invention can include means for amplification of the HPRT gene which is independent of replication of the viral genome. Expression of the human HPRT gene can thus be enhanced in either replication-competent or replication-defective vectors of the invention. The recombinant viral vector is provided with a nonviral initiation site of DNA synthesis which allows autonomous replication and amplification of the HPRT minigene. An autonomous replicating sequence (ARS), such as that described in Ariga, H. et al., "Autonomous Replicating Sequences from Mouse Cells which can Replicate in Mouse Cells In Vivo and In Vitro", *Mol. Cell. Biol.*, Vol. 7, No. 1, pp. 1–6 (1987), is operatively linked to the HPRT minigene to produce an autonomously replicating "minigene cartridge". The minigene cartridge is recombined with the appropriate HSV-1 genome to produce a recombinant HSV-1 carrying the cartridge. The nonviral initiation site will allow the minigene cartridge containing the ARS and HPRT minigene to replicate independently of the vital genome of the vector and to amplify especially within the host cell.

SPECIFIC EXAMPLES

Example 1

Referring now to the Figure, a schematic representation of the construction of a recombinant HSV-1 vector carrying the viral TK promoter and human HPRT cDNA, i.e. the HPRE minigene, is shown. As shown in the Figure, and described in more detail below, plasmid pX1 is constructed by cloning the BamH1 Q fragment of HSV-1, which contains the viral TK gene and promoter, into the BamH1 site of *E. Coli* plasmid pBR 322. Plasmid pX1 is then linearized by restriction endonuclease Bgl-II. A 950-base pair fragment containing the human HPRT cDNA is blunt-ended, ligated to BamH1 linkers, and the fragment then ligated to the linearized pX1. The recombinant plasmid which contains one copy of the HPRT cDNA in the sense orientation (proper reading frame), designated pX1-HP40, is isolated, linearized and recombined with the intact wild type HSV-1 genome by cotransfection of Vero cells. As shown in the Figure, recombinant HSV-1 carrying the HPRT minigene are isolated by plaque hybridization with labeled EPRT cDNA and plaque purified. Expression of human HPRT activity in HPRT rat neuronal cells infected by recombinant HSV-HP40 containing the sense orientation of the HPRT gene is near or above normal levels of expression in HPRT⁺ cells, yet the viral vector construct exhibits a mild to moderate reduction of cytopathicity due to the position of insertion of the recombinant plasmid into the TK gene of the HSV-1 wild type genome.

A. Construction of Recombinant HPRT/HSV-1 Vector

1. Viral TK Promoter

The HSV-1 thymidine kinase (TK) gene is contained within a 3,560-base-pair BamH1 fragment of the HSV-1 genome, BamH1 Q. Plasmid pX1, which results from the cloning of the HSV BamH1 Q fragment (map units 0.293 and 0.316) into the BamH1 site of pBR322 is known and available and is described in Enquist, L. W., et al., "Construction and Characterization of a Recombinant Plasmid Encoding the Gene for the Thymidine Kinase of Herpes Simplex Type 1 Virus", *Gene*, Vol. 7, pp. 335–342 (1979). Plasmid pX1 has a single BglII site, located within the 5'-transcribed noncoding region of the HSV TK gene.

2. Human HPRT Gene

The human HPRT cDNA used in this construct, a 950-base-pair fragment including 100 base pairs of 5' untranslated sequence and 200 base pairs of 3' untranslated sequence, is known and available and is described in Brennand, J., et al., "Expression of Human and Chinese Hamster Hypoxanthine-Guanine Phosphoribosyltransferase cDNA Recombinants in Cultured Lesch-Nyhan and Chinese Hamster Fibroblasts", *J. Biol. Chem.*, Vol. 258, pp. 9593–9596 (1983). Synthetic BamH1 linkers were ligated to the blunt-ended HPRT cDNA, and excess linkers digested with BamH1.

3. Construction of HPRT Minigene

Plasmid pX1 was linearized with BglII and ligated to the BamH1-digested HPRT cDNA fragment. The recombinant plasmid was amplified by transfection of *E. coli* DH1. Plasmid DNA was digested with HamH1 and subjected to Southern blot analysis with $^{32}$P-labeled HPRT cDNA as a probe to confirm the presence of HPRT sequences. These plasmids were then digested with HincII to determine the sense or antisense orientation of the HPRT cDNA with respect to the TK promoter. Two plasmids, each of which contained a single copy of HPRT cDNA, and which were designated pX1-HP40 and pX1-PIP87, contained the cDNA insert in the sense and antisense orientations, respectively.

4. Construction and Isolation of Recombinant Viral Vector

Chimaeric virus was isolated following cotransfection of Vero cells by calcium phosphate precipitation with 2 µg of a BamH1 digest of either pX1-EP40 or pX1-HP87, 0.5 µg of intact HSV-1 KOS DNA, and 7 µg of calf thymus DNA as a carrier. On day 3 posttransfection, virus was harvested by repeated freeze-thaw cycles. Dilutions of this lysate were used to infect confluent Vero cell monolayers which were overlaid with 1% agarose and incubated at 37° C. for 3 days, at which time plaques appeared. Plaques were blotted onto nitrocellulose from the underside of the agarose, denatured, and hybridized to $^{32}$P-labeled HPRT cDNA as previously described by Homa, F. L., et al., "Transcriptional Control Signals of a Herpes Simplex Virus Type 1 Late ($\gamma_2$) Gene Lie within Bases −34 to +124 Relative to the 5′ Terminus of the mRNA", *Mol. Cell. Biol.*, Vol. 6, pp. 3652–3666 (1986). Plaques giving positive signals were picked, and virus was plaque purified three times. Two recombinant viruses were isolated: HSV-HP40, in which HPRT cDNA is in the sense orientation with respect to the TK promoter sequences, and HSV-HP87, in which HPRT cDNA is in the antisense orientation with respect to the TK promoter.

Viral DNA extracted from cells infected with HSV-HP40 and HSV-HP87 was digested with BamH1 and analyzed by Southern blotting to determine the site of insertion of the HPRT cDNA into the HSV genome as well as the number of copies incorporated. Viral DNA extracted from wild type HSV-1 KOS, HSV-HP40, and HSV-HP87 was digested with BamHI and these digests as well as the BamH1 Q fragment electrophoresed in 1.2% agarose gels. BamH1 Q, approximately 3.5 kilobases in length, was present in the HSV-1 KOS control. This band was not present for HSV-PIP40 and HSV-HP87, but a new band of approximately 4.5 kilobases appeared, corresponding to the Q′ fragments of pxl-HP40 and pX1-EP87. This is consistent with incorporation of a single copy of HPRT cDNA into each recombinant virus.

Southern blot analysis of Bam digestion from a blot of the electrophoretic gel was conducted by hybridizing one set of the electrophoresed BamH1 Q fragment and BamH1 digests of HSV-KOS, HSV-EP40 and HSV-HP98 with a $^{32}$P-labeled Pst1 fragment of the HSV TK gene, and hybridizing a second set with a $^{32}$P-labeled Pst1 fragment of human HPRT cDNA. TK sequences hybridized to the BaMH1 Q fragment of HSV-1 KOS and to the BamH1 Q′ fragments of HSV-HP40 and HSV-HP87. No HPRT hybridization signal was detected in HSV-1 KOS. HPRT cDNA hybridized to the BamH1 Q′ fragments of HSV-HP40 and HSV-HP87. Furthermore, HPRT cDNA remained associated with the viral TK sequences as expected.

B. Expression of HPRT Activity

1. Neuronal Cell Line

Infections were performed in an HPRT$^-$ derivative of rat neuroma cell line B103. B103 cells were rendered HPRT$^-$ by $^{60}$Co-irradiation-induced mutagenesis and selection in 14 µg of 6-thioguanine per ml. HPRT deficiency was confirmed by radioisotopic assay for HPRT and by demonstration of nonviability in HAT medium (110 µM hypoxanthine, 2.3 µM aminopterin, 20 µM thymidine). The HPRT$^-$ clone used in these studies was designated B103-4C.

2. Expression of Human HPRT Activity in Culture

B103-4C cells in confluent monolayers were infected with HSV-HP40 and HSV-EP87 at a multiplicity of infection of 4. Uninfected B103-4C cells and B103-4C cells infected with HSV-1 KOS were used as controls. Cells were harvested at 6, 20, and 30 h and lysed by repeated freezing and thawing. Cellular debris was removed by centrifugation, and the extracts were assayed for HPRT by determining conversion of [8-$^{14}$C]hypoxanthine to [8-$^{14}$C]IMP as described in Holden, J. A. et al., "Human Hypoxanthine-Guanine Phosphoribosyl transferase: Evidence for Tetrameric Structure, *J. Biol. Chem.*, Vol. 253, pp. 4459–4463 (1975). Results of these experiments are shown in Table 1.

TABLE 1

Expression of HPRT activity in virus-infected B103-4C cells[c]

| HPRT virus[b] | Postinfection HPRT activity (nmol min per mg of protein) at: | | |
|---|---|---|---|
| | 6 h | 20 h | 30 h |
| HSV-HP40 (sense orientation) | 0.07 | 9.60 | ND |
| | 0.04 | 4.38 | 2.32 |
| | 0.04 | 1.36 | 1.85 |
| | 0.04 | 5.01 | ND |
| HSV-HP87 (antisense orientation) | 0.29 | 1.30 | ND |
| | 0.16 | 0.46 | 0.30 |
| | 0.20 | 0.97 | 0.75 |
| | 0.15 | 0.87 | ND |

[a]HPRT activity in wild-type B103 cells was 2.80 = 0.35 nmol/min per mg (n = 8); in B103-4C cells it was <0.04 (n = 8); and in HSV-1 KOS-infected B103-4C cells (at 6, 20, and 30 h) it was <0.04 (n = 6).
[b]Multiplicity of infection was 4.
[c]Data in each column were obtained from four separate experiments. Each value represents the mean of at least four assays. The lower limit of sensitivity for the HPRT assay is 0.04 nmol/min per mg of protein. ND, Not determined.

No HPRT activity was detectable in uninfected B103-4C cells or in HSV-1 KOS-infected B103-4C cells. In cells infected with HSV-HP40, HPRT activity was barely detectable at 6 h, but the levels rose significantly at 20 and 30 h. HPRT activity was also detected in HSV-HP87-infected cells at all three time points; compared with levels in HSV-HP40-infected cells, activity in HSV-HP87-infected cells was higher at 6 h and lower but significant at 20 and 30 h.

3. Determination of Origin of HPRT

To determine the origin (rat versus human) of the expressed HPRT activity in each experimental condition, cell extracts were electrophoresed through 6% polyacrylamide gels under nondenaturing conditions. Replicate gels were subjected to autoradiographic assay for HPRT activity in situ and to immunoblot analysis with polyclonal anti-human HPRT antiserum having no detectable cross-reactivity with rat HPRT.

(a) Autoradiographic Assay

Human HPRT activity was detected by autoradiography only in normal human lymphoblast cell line GM-558 and in B103-4C cells infected with HSV-HP40. Rat HPRT enzyme, which migrates faster than human HPRT enzyme, was detected only in wild-type B103 cell extracts. HPRT activity in situ was determined by incubation of a 6% polyacrylamide gel in a substrate solution containing 100 mM Tris (pH 7.4). 10 mM MgCl$_2$, 10 mM PRPP, and 72 µM [8-$^{14}$C] hypoxanthine (45 ° C. µCi/µmol) for 30 min. The gel was then adsorbed onto polyethylene/nine cellulose, which binds [8-$^{14}$C]IMP, but not hypoxanthine or inosine. The polyethyleneimine cellulose was washed in water, dried, and exposed to X-ray film at −70° C. for 1 week as described in Zannis, V. I. et al., "Characterization of the Subunit Composition of HGPRTase from Human Erythrocytes and Cultured Fibroblasts," *Biochem. Genet.*, Vol. 18, pp. 1–19 (1980).

GM 558, a normal human lymphoblast line and HSV-HP40-infected B103-4C cells (20 h postinfection) shooed normal human HPRT activity. Wild-type B103 cells showed normal rat HPRT activity. No HPRT activity was detected in lysates of HSV-HP87 or HSV-1 KOS-infected B103-4C cells (20 h postinfection). A broad smear of activity with a higher apparent molecular weight than that of human HPRT was detected by this method for lysates of HSV-EP87-infected cells. MPEr activity in these cells may represent a fusion protein, the expression of which is under the control of a different promoter than that of HSV TK. However, HPRT activity from HSV-HP40-infected cells clearly comigrated with human HPRT.

(b) Immunoblot Analysis

Further evidence that the HPRT activity detected in HSV-HP40-infected cells was of human origin was provided by immunoblot analysis by the methods described in Wilson, J. M. et al., "Human Hypoxanthine-Guanine Phosphoribosyl-transferase: Purification and Characterization of Mutant Forms of the Enzyme", *J. Biol. Chem.*, Vol. 256, pp. 10306–10312 (1983). Human HPRT protein was present only in extracts from GM 558 cells and HSV-HP40-infected B103-4C cells.

After electrophoresis, proteins were electroblotted onto nitrocellulose filters. Filters were prehybridized with BLOTTO (1% Carnation powdered milk in 10 mM Tris [pH 7.4] and 150 mM NaCl), incubated with rabbit anti-human HPRT antiserum which has no detectable cross reaction with rat HPRT, and probed with [$^{125}$I]Staphylococcus protein A. Blots were washed, dried, and exposed overnight to Kodak XR-5 film at $-70°$ C. Extracts of 6M 558 cells and HSV-HP40-infected B103-4C cells (20 h postinfection) contained material that reacted immunologically with anti-human HPRT antiserum and comigrated with human HPRT activity. No reaction was noted in B103, HSV-HP87- or HSV-KOS-infected B103-4C (20 h postinfection), or B103-4C cell lysates.

4. Cytopathicity of Recombinant HSV-1

The recombinant vectors used in this study exhibited a moderate to mild reduction in cytopathicity. At 20 h postinfection, approximately 90% of HSV-EP40-infected cells and 70% of HSV-EP87-infected cells survived while only 50% of HSV-1 KOS-infected cells were still viable. At 30 h postinfection, however, the cytopathic effects of all three vectors were more pronounced, with approximate viability rates of 60, 50, and 25% for HSV-HP40-, HSV-HP87-, and HSV-1 KOS-infected cells, respectively.

5. Transformation of Cells in Culture

Transformation of HPRT$^-$ rat neuronal cells was also attempted to achieve stable expression of the human HPRT gene. Transformation resulted in about one out of one thousand HPRT$^-$ rat neuronal cells infected with HSV-HP40 continuing to survive in HAT medium for over four months postinfection.

Example 2

Reduction of virulence of the HSP-HP40 vector construct carrying the HPRT minigene was accomplished by UV-irradiating the vector, then selecting for replication-defectiveness as described in Munyon, et al. "Transfer of Thymidine Kinase to Thymidine Kinaseless L cells by Infection with Ultraviolet-irradiated Herpes Simplex Virus", *J. Virol.*, Vol. 7, pp. 813–820 (1971) and as detailed below.

A) Construction of UV-Irradiated Replication Defective HPRT/HSV-1 Recombinant Vector 1. Cell and Virus Cultures B103-4C neuronal cells obtained as described in Specific Example 1 were maintained in Dulbecco Modified Eagle Medium (MEM) containing 10% fetal calf serum (PCS) and 14 μg/ml 6-thioguanine. HSV-HP40 and HSV-HP87 obtained as described in Specific Example 1 were stored at $-70°$ C. in MEM containing 10% FCS and 10% glycerol.

2. Ultraviolet Irradiation of Virus and Infection of B103-4C Cells

Stock suspensions of HSV-BP40 or HSV-PIP87 ($3 \times 10^7$ plaque forming units per milliliter) were exposed to ultraviolet (UV) radiation at UV intensity of 23 ergs per mm$^2$ per second in the manner described in Munyon, et al., "Transfer of Thymidine Kinase to Thymidine Kinaseless L Cells by Infection with Ultraviolet-irradiated Herpes Simplex Virus", *J. Virol.* Vol. 7, pp. 813–820 (1971). UV dose was varied as a function of the duration of exposure to UV light. Vital replicating capacity was assayed by determination of plaque forming units (pfu) as described in Manyon, et al. Those suspensions yielding no plaques (0 pfu) were used in the subsequent infection.

Monolayers of B103-4C cells ($1 \times 10^5$ cells per 60 mm petri dish) were infected with 0.2 ml of the UV irradiated vital stock suspension and incubated at $37°$ C. After one hour, the inoculum was aspirated and 5 ml of MEM containing 10% FCS was added to each dish. After 24 hours, the medium was replaced with HAT (hypoxanthine 110 μM, aminopterin 2.3 μM, thymidine 20 μM) medium, which was replaced every 48 hours. Surviving HPRT$^+$ colonies of cells were isolated after 14 days and expanded.

3. HPRT Enzyme Analysis

Protein from the HAT resistant colonies (HPRT$^+$) is prepared from $5 \times 10^6$ to $5 \times 10^7$ cells. Cells are suspended in 10 mM Tris HCl (pH 7.4) and lysed by 5 cycles of freezing and thawing. Cellular debris is removed by centrifugation at 38,000 rpm for 45 minutes and the supernatant is dialyzed overnight against 10 mM Tris HCl (pH 7.4), 150 mM sodium chloride. HPRT activity is determined by radioisotopic assay using $^{14}$C-hypoxanthine as the substrate as described in Specific Example 1. To determine rat versus human origin of HPRT activity, in situ activity staining and immunoblotting is also performed as described in Specific Example 1.

4. DNA Analysis

High molecular weight DNA is isolated from HAT resistant B103-4C cells as previously described in Sandri-Goldin, R. M. et al., "Expression of Herpes Simplex Virus B and Y Genes Integrated in Mammalian Cells and their Induction by an alpha Gene Product", *Mol. Cell. Biol.*, Vol. 3, pp. 2028–2044 (1983). DNA is digested using restriction enzymes and electrophoresed on agarose gels and the DNA transferred to nitrocellulose as previously described and probed with $^{32}$P labeled HPRT cDNA using the techniques set out in Southern, E. M. et al., "Detection of Specific Sequences Among DNA Fragments separated by Gel Electrophoresis", *J. Mol. Biol.*, Vol. 98, pp. 503–517 (1975).

Example 3

To further reduce the virulence of the HSV-HP40 construct described above, a replication-defective vector derived from an HSV-1 deletion mutant was constructed. As described more specifically below, the BamH1 digest of pX1-HP40, which contains the HPRT minigene in the sense orientation, was recombined with an HSV-1 replication-defective mutant having a deletion in the α4 gene (which produces ICP4 necessary to initiate viral replication) through cotransfection of the E5 Vero-derived cell line which expresses and supplies ICP4 in trans to the replication-defective viruses.

A. Construction of Replication-Defective Recombinant HSV-d120

1. Cell and Virus Cultures

Replication-defective d120, a herpes simplex virus type 1 (HSV-1) mutant which contains a 4.1 kilobase deletion in each copy of the α4 gene. The α4 gene codes for ICP4 which is necessary for imitation of viral synthesis. Vero-derived E5 cells, which express ICP4 in trans were used as the packaging cell line. E5 cells were maintained in Dulbecco Modified Eagle Medium (MEM) containing 5% fetal calf serum (FCS). Both the d120 mutant and the E5 cell line are known and available and are described in DeLuca, N. A., et al., "Isolation and Characterization of Deletion Mutants of Herpes Simplex Virus Type 1 in the Gene Encoding Immediate Early Regulations Protein ICP4", *J. Virol.*, Vol. 56, pp. 558–570 (1985).

2. Plasmids pX1-HP40 described in Specific Example 1, was used in this construct. pX1-HP40 contains the Bam-H1 Q fragment of HSV 1 into which has been cloned a 950-base pair human HPRT cDNA within the 5'-transcribed noncoding region of the viral thymidine kinase gene.

3. Cotransfection

Two μl of a Bam-H1 digest of pX1-HP40 and 0.5 μg pf intact d120 DNA were added to 0.6 ml of HEPES buffered saline pH 7.1. After cooling on ice, 41 μl of cold 2M calcium chloride was added. After 30 minutes at room temperature, the DNA solution was added to a 50 mm petri dish containing a confluent monolayer of E5 cells and incubated at 37° C. Five ml of MEM containing 5% FCS was added after 40 minutes and the cells again incubated at 37° C. for an additional 4 hours. The medium was then aspirated. 1.5 ml of 25% DMSO in HBS was slowly added and then aspirated after 4 minutes. Cells were washed with medium three times. Five ml of medium was added and the cells again incubated at 37° C.

Five to seven days posttransfection, virus was harvested by repeated cycles of freezing and thawing. Dilutions of this lysate were used to infect E5 cell monolayers which were overlayed with 1.2% agarose and incubated for 5–7 days at which time plaques formed. Plaques were blotted onto nitrocellulose, denatured and hybridized to $^{32}$p labeled HPRT cDNA as previously described in Homa, F. L. et al., "Transcriptional Control Signals of a Herpes Simplex Virus Type 1 Late y2 Gene Lie Within Bases –34 to =124 Relative to the 5' Terminus of the mRNA", *Mol. Cell. Biol.*, Vol. 6, pp. 3652–3666 (1986). Plaques that hybridized to labeled. HPRT cDNA were picked and virus plaque purified three times.

Example 4

HPRT/HSV-1 recombinant viral vector constructs were provided with means for vital replication-independent amplification of the HPRT gene by incorporating a nonviral initiation site of DNA synthesis into the vector as detailed below. An ARS sequence carried on the plasmid p65 as described by Ariga, H. et al; "Autonomous Replicating Sequences From Mouse Cells Which Can Replicate in-Mouse Cells in Vivo and in Vitro" *Mol. Cell. Biol.*, Vol. 7, pp. 1–6 (1987), was cloned into the EcoR1 site of pX1-HP40 which carries the HPRT minigene. The resultant recombinant plasmid, designated pXHA, containing the HPRT minigene and the ARS sequence, i.e. the minigene cartridge, and intact DNA derived from HSV-1 KOS (wild type strain) were then recombined by cotransfection of Vero cells. An analogous replication-defective vector was also constructed by recombining pXHA with DNA from the replication-defective α4 HSV-1 mutant in the E5 packaging cell line as described in specific Example 3.

A. Construction of HSV/ARS/HPRT Recombinant Vectors

1. ARS/HSV Plasmid

The plasmid p65, consists of pKB111 and the 2.5-kb autonomous replicating sequence (ARS) from mouse cells was used to construct HSV-1 vectors with a nonviral site of initiation of DNA synthesis. The ARS sequence and p65, which are known and available, are described in Ariga, H. et al., "Autonomous Replicating Sequences from Mouse Cells which can Replicate in Mouse Cells In Vivo and In Vitro", *Mol. Cell. Biol.*, Vol. 7, pp. 1–6 (1987).

The 2.7-kb EcoR1-Bgl-II fragment containing ARS obtained from p65 was excised, blunt ended, ligated with EcoR1 linkers and cloned into one of three EcoR1 sites of pX1-HIP40. The EcoR1 site in pX1-HP40 used for cloning was located in the sequence derived from HSV, 1.1-kb downstream from the termination codon of thymidine kinase (TK) coding sequence. The resultant plasmid containing the ARS fragment was designated pXHA. An alternative site into which ARS has also been inserted into the Kpn 1 site in pX1-EP40. This site is approximately 0.5-kb upstream from the viral TK start codon.

2. Construction of HSV-KOS/ARS/HRPT and HSV-d120/ARS/HRPT Vectors

The plasmid pXHA was used for cotransfection of Vero cells with DNA derived from HSV type 1 strain KOS, as described in Specific Example 1, or with HSV type 1 strain d120 for cotransfection of E5 cells, as described in Specific Example 3. Viral isolation and purification proceeds as described in Specific Example 1.

It is apparent that many modifications and variations of this invention as set forth as may be made without departing from the spirit and scope thereof. The specific embodiments described herein are given by way of example only and the invention is limited only by the terms of the appended claims.

What is claimed is:

1. A vector for direct delivery of a gene to a mammalian host comprising a recombinant viral vector which targets and expresses a mammalian gene in a selected cell in the mammalian host, the recombinant vector further comprising:

a) at least a portion of the genome of a DNA virus which exhibits tropicity for the selected host cell, which portion is operatively arranged to infect the host cell, wherein the portion of the genome is modified to have a level of virulence less than the level of virulence present in a virulent wild type viral strain from which the recombinant viral vector is derived; and b) a mammalian gene operatively linked to the portion, wherein the operatively-linked gene is expressed in the host cell after infection of the cell.

2. The recombinant vector of claim 1, wherein the DNA virus is a double-stranded neurotropic virus, the gene is a gene for human hypoxanthine-guanine phosphoribosyltransferase, and the vector further comprises a promoter sequence of DNA for promoting expression of the gene.

3. The recombinant vector of claim 1, wherein the portion of the viral genome is replication-defective.

4. The vector of claim 1, wherein the DNA virus is a latent virus.

5. The vector of claim 1, wherein the DNA virus is a herpes simplex virus.

6. The vector of claim 1, wherein the gene is a therapeutic gene.

7. A method for expressing a mammalian gene which comprises infecting a cell with the vector of claim 1 under conditions suitable for the expression of the mammalian gene.

8. A host cell comprising the vector of claim 1.

9. The recombinant vector of claim 2, wherein the DNA virus is herpes simplex virus and the vector is synthesized by a process comprising:
   a) cloning a fragment comprising a herpes simplex virus type 1 thymidine kinase promoter into a suitable plasmid;
   b) linearizing the plasmid with Bgl II to obtain linear plasmid DNA;
   c) obtaining a fragment comprising human HPRT cDNA, and blunt-ending and ligating the fragment to BamH1 linkers to form a ligatable fragment;
   d) ligating the ligatable fragment to the linear plasmid DNA to form a recombinant plasmid containing a TK promoter-HPRT minigene;
   e) linearizing and recombining the recombinant plasmid with an intact wild-type herpes virus genome to form recombinant viral progeny containing the TK promoter-HPRT minigene.

10. A method of targeted viral-mediated transfer and expression of a nonviral gene in a selected cell of a host organism comprising the steps of:
   a) selecting a DNA virus infectious for the host organism and exhibiting tropicity for the selected cell;
   b) providing at least a portion of the genome of the DNA virus, wherein the portion is operatively arranged to infect the host organism;
   c) operatively linking the nonviral gene to the portion to form a recombinant viral vector, the operatively-linked gene being expressed in the selected cell after infection of the host organism by the vector;
   d) modifying the DNA viral genome or the portion selected thereof to have a level of virulence less than the level of virulence present in a wild type virulent strain from which the portion of the genome is derived; and
   e) infecting the host organism with a sufficient quantity of the viral vector under conditions suitable for the transfer and expression of the non-viral gene in the cell.

11. The method of claim 10, wherein the portion of the genome of the virus is replication-defective.

12. The method of claim 10, wherein the DNA virus is a latent virus.

13. The method of claim 10, wherein the DNA virus is a herpes simplex virus.

14. The method of claim 10, wherein the gene and host are mammalian.

15. The method of claim 10, wherein the nonviral gene is a therapeutic gene.

16. The method of claim 11, wherein the virus is a double-stranded neurotropic virus.

17. The method of claim 16, wherein the virus is a herpes simplex virus, the gene is A gene for hypoxanthineguanine phosphoribosyltransferase, and the recombinant vector further comprises a viral promoter sequence for promoting expression of the gene.

18. The method of claim 14, wherein the gene is a human gene.

19. A recombinant viral vector which expresses a mammalian gene in a selected mammalian host cell comprising:
   a) at least a portion of the genome of a DNA virus selected for tropicity for the selected host cell, which portion is operatively ganged to infect the host cell, wherein the portion of the genome is modified to have a level of virulence less than the level of virulence present in a virulent wild type viral strain from which the vector is derived; and
   b) a mammalian gene operatively linked to the portion and wherein the operatively linked gene is expressed in the host cell after infection of the cell.

20. The recombinant vector of claim 19, wherein the DNA virus is a double-stranded neurotropic virus, the gone is a gone for human hypoxanthine-guanine phosphoribosyltransferase, and the vector further comprises a promoter sequence of DNA for promoting expression of the gone.

21. The vector of claim 19, wherein the DNA virus is a latent virus.

22. The vector of claim 19, wherein the DNA virus is a herpes simplex virus.

23. A method for expressing a mammalian gene which comprises infecting a cell with the vector of claim 14 under conditions suitable for the expression of the mammalian gene.

24. A host cell comprising the vector of claim 19.

25. The recombinant vector of claim 20, wherein the DNA virus is herpes simplex virus and the vector is synthesized by a process comprising:
   a) cloning a fragment comprising a herpes simplex virus type 1 thyroidine kinase promoter into a suitable plasmid;
   b) linearizing the plasmid with Bgl II to obtain linear plasmid DNA;
   c) obtaining a fragment comprising human HPRT cDNA, and blunt-ending and ligating the fragment to BamH1 linkers to form a ligatable fragment;
   d) ligating the ligatable fragment to the near plasmid DNA to form a recombinent plasmid containing a TK promoter-HPRT minigene; and
   e) linearizing and recombining the recombinant plasmid with an intact wild-type herpes virus genome to form recombinant vital progeny containing the TK promoter-HPRT minigene.

26. The recombinant vector of claim 20, wherein the portion of the viral genome is replication-defective.

27. A method of viral-mediated transfer and expression of a mammalian gene in a selected cell of a mammalian host organism comprising the steps of:
   a) selecting a DNA virus infectious for the host organism and exhibiting tropicity for the selected cell;
   b) providing at least a portion of the genome of the DNA virus, wherein the portion is operatively ganged to infect the host organism;
   c) operatively linking the gene to the portion to form a recombinant viral vector, the operatively-linked gene being expressed in the selected cell after infection of the host organism by the vector;

d) modifying the recombinant viral vector to have a, level of virulence less than that present in a wild type virulent strain from which the portion of the genome is derived; and e) infecting the host organism with a sufficient quantity of the viral vector under conditions suitable for the transfer and expression of the mammalian gene in the cell.

28. The method of claim 27, wherein the portion of the genome of the virus is replication-defective.

29. The method of claim 27, wherein the DNA virus is a latent virus.

30. The method of claim 27, wherein the DNA virus is a herpes simplex virus.

31. The method of claim 28, wherein the virus is a double-stranded neurotropic virus and further comprises an autonomous replicating sequence of mammalian origin.

32. The method of claim 31, wherein the virus is a herpes simplex virus, the gene is a gene for hypoxanthine-guanine phosphorlbosyltransferase, and the recombinant vector further comprises a vital promoter sequence for promoting expression of the gene.

33. The method of claim 27, wherein the gene is a human gene.

34. The method of claim 7, wherein the nonviral gene is a therapeutic gene.

35. The method of claim 23, wherein the nonviral gene is a therapeutic gene.

* * * * *

UNITED STATES PATENT AND TRADEMARK OFFICE
CERTIFICATE OF CORRECTION

PATENT NO. : 5,672,344

DATED : September 30, 1997

INVENTOR(S) : Willliam N. Kelley, Thomas D. Palella and Myron Levine

It is certified that error appears in the above-identified patent and that said Letters Patent is hereby corrected as shown below:

On the title page item [57],

Abstract, line 9, the word "vital" should be --viral--

Column 1, line 4, insert the paragraph "This invention was made with government support under Grant No. DK39834 awarded by the National Institute of Diabetes and Digestive and Kidney Diseases of the National Institutes of Health. The government may have certain rights in this invention."

Column 1, line 4, delete the word "division"

Column 2, line 23, the word "retrovital" should be --retroviral--

Column 3, line 4, the word "EPRT" should be --HPRT-- line 5, the word "RPRT" should be --HPRT--

Column 4, line 66, the word "nonlyric" should be --nonlytic--

UNITED STATES PATENT AND TRADEMARK OFFICE
CERTIFICATE OF CORRECTION

PATENT NO. : 5,672,344

DATED : September 30, 1997

INVENTOR(S) : Willliam N. Kelley, Thomas D. Palella and Myron Levine

It is certified that error appears in the above-identified patent and that said Letters Patent is hereby corrected as shown below:

Column 5, line 1, the word "Elian" should be --mammalian-- line 18, the word "vital" should be --viral-- line 25, the word "Veto" should be --Vero-- line 27, the word "EPRT" should be --HPRT-- line 66, the word "vital" should be --viral-- line 67, the word "especially" should be --episomally--

Column 6, line 7, the word "HPRE" should be --HPRT-- line 23, the word "HPRT" (second occurrence) should be --HPRT⁻-- line 63, the word "HamH1" should be --BamH1--

Column 7, line 36, the word "HSV-PIP40" should be --HSV-HP40-- line 38, the word "px1-HP40" should be --pX1-HP40-- line 39, the word "pX1-EP87" should be --pX1-HP87-- line 44, the word "HSV-EP40" should be --HSV-HP40--

UNITED STATES PATENT AND TRADEMARK OFFICE
CERTIFICATE OF CORRECTION

PATENT NO. : 5,672,344

DATED : September 30, 1997

INVENTOR(S) : Willliam N. Kelley, Thomas D. Palella and Myron Levine

It is certified that error appears in the above-identified patent and that said Letters Patent is hereby corrected as shown below:

line 47, the word "BaMH1" should be --BamH1-- line 67, the word "HSV-EP87" should be --HSV-HP87--

Column 8, lines 7 and 8, the words "Phosphoribosyl transferese" should be --Phosphoribosyltransferase-- line 55, the word "GM-558" should be --GM558-- line 63, the word "polyethylene/nine" should be --polyethyleneimine--

Column 9, line 5, the word "shooed" should be --showed-- line 11, the word "HSV-EP87-"should be --HSV-HP87-- line 12, the word "MPEr" should be --HPRT-- line 34, the word "6M" should be --GM-- line 44, the word "HSV-EP40-infected" should be --HSV-HP40-infected-- line 45, the word "HSV-EP87-infected" should be --HSV-HP87-infected--

UNITED STATES PATENT AND TRADEMARK OFFICE
CERTIFICATE OF CORRECTION

PATENT NO. : 5,672,344

DATED : September 30, 1997

INVENTOR(S) : Willliam N. Kelley, Thomas D. Palella and Myron Levine

It is certified that error appears in the above-identified patent and that said Letters Patent is hereby corrected as shown below:

Column 10, line 7, the word "(PCS)" should be --(FCS)-- line 13, the word "HSV-BP40" should be --HSV-HP40-- line 13, the word "HSV-PIP87" should be --HSV-HP87-- line 20, the word "vital" should be --viral-- line 27, the word "vital" should be --viral--

Column 11, line 51, the word "$^{32}p$" should be --$^{32}P$-- line 55, the word "5'Terminus" should be --5' Terminus-- line 56, the punctuation "." should be deleted line 62, the word "vital" should be --viral--

Column 12, line 1, the word "in-Mouse" should be two words --in Mouse--

Column 13, line 63, after the word "and" insert the word --the--

Column 14, line 4, the word "A" should be --a-- line 4, the word "hypoxanthineguanine" should be --hypoxanthine-guanine-- line 14, the word "ganged" should be --arranged--

UNITED STATES PATENT AND TRADEMARK OFFICE
CERTIFICATE OF CORRECTION

PATENT NO. : 5,672,344

DATED : September 30, 1997

INVENTOR(S) : Willliam N. Kelley, Thomas D. Palella and Myron Levine

Page 5 of 6

It is certified that error appears in the above-identified patent and that said Letters Patent is hereby corrected as shown below:

line 23, the word "gone" should be --gene-- line 24, the word "gone" should be --gene-- line 27, the word "gone" should be --gene-- line 33, the number "14" should be --19-- line 41, the word "thyroidine" should be --thymidine-- line 48, the word "near" should be --linear-- line 49, the word "recombinent" should be --recombinant-- line 53, the word "vital" should be --viral-- line 63, the word "ganged" should be --arranged--

Column 15, line 3, the punctuation "," should be deleted line 4, the word "that" should be --the level of virulence--

UNITED STATES PATENT AND TRADEMARK OFFICE
CERTIFICATE OF CORRECTION

PATENT NO. : 5,672,344

DATED : September 30, 1997

INVENTOR(S) : Willliam N. Kelley, Thomas D. Palella and Myron Levine

It is certified that error appears in the above-identified patent and that said Letters Patent is hereby corrected as shown below:

Column 16, line 6, the word "phosphorlbosyltransferase" should be

--phosphoribosyltransferase-- line 7, the word "vital" should be --viral--

Signed and Sealed this

Thirty-first Day of March, 1998

Attest:

BRUCE LEHMAN

Attesting Officer

Commissioner of Patents and Trademarks